(12) United States Patent
Choi

(10) Patent No.: US 9,783,562 B2
(45) Date of Patent: Oct. 10, 2017

(54) PHYTOSPHINGOSINE-1-PHOSPHATE DERIVATIVE, PREPARATION METHOD THEREFOR, AND COMPOSITION FOR PREVENTING AND TREATING HAIR LOSS OR FOR GROWING HAIR COMPRISING SAME

(71) Applicant: PHYTOS CO., LTD., Suwon-si, Gyeonggi-do (KR)

(72) Inventor: Myeong Jun Choi, Seoul (KR)

(73) Assignee: PHYTOS CO., LTD, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/781,638

(22) PCT Filed: Apr. 4, 2013

(86) PCT No.: PCT/KR2013/002789
§ 371 (c)(1),
(2) Date: Oct. 1, 2015

(87) PCT Pub. No.: WO2014/163219
PCT Pub. Date: Oct. 9, 2014

(65) Prior Publication Data
US 2016/0046656 A1  Feb. 18, 2016

(51) Int. Cl.
| | | |
|---|---|---|
| *C07F 9/6584* | (2006.01) | |
| *C07F 9/6574* | (2006.01) | |
| *C07F 9/09* | (2006.01) | |
| *C07F 9/141* | (2006.01) | |
| *C07F 9/24* | (2006.01) | |
| *A61K 8/14* | (2006.01) | |
| *A61K 8/55* | (2006.01) | |
| *A61Q 5/02* | (2006.01) | |
| *A61Q 5/12* | (2006.01) | |
| *A61Q 7/00* | (2006.01) | |
| *A61Q 19/08* | (2006.01) | |

(52) U.S. Cl.
CPC ........... *C07F 9/65844* (2013.01); *A61K 8/14* (2013.01); *A61K 8/55* (2013.01); *A61Q 5/02* (2013.01); *A61Q 5/12* (2013.01); *A61Q 7/00* (2013.01); *A61Q 19/08* (2013.01); *C07F 9/091* (2013.01); *C07F 9/1411* (2013.01); *C07F 9/2408* (2013.01); *C07F 9/65742* (2013.01); *C07F 9/65846* (2013.01)

(58) Field of Classification Search
None
See application file for complete search history.

(56) References Cited

PUBLICATIONS

Boumendjel et al., "Synthesis of sphingosine-1-phosphate and dihydrosphingosine-1-phosphate", Journal of Lipid Research, vol. 35, pp. 2305-2311, (1994).
Nagiec et al., "The LCB4 (YOR171c) and LCB5 (YLR260w) Genes of *Saccharomyces* Encode Sphingoid Long Chain Base Kinases", The Journal of Biological Chemistry, vol. 273, No. 31, pp. 19437-19442, (1998).
Pyne et al., "Sphingosine 1-phosphate signalling in mammalian cells", Biochem. J., vol. 349, pp. 385-402, (2000).
Lee et al., "Sphingosine-1-Phosphate as a Ligand for the G Protein-Coupled Receptor EDG-1", Science, vol. 279, pp. 1552-1555, (1998).
Szulc et al., "A facile regioselective synthesis of sphingosine 1-phosphate and ceramide 1-phosphate", Tetrahedron Letters, vol. 41, pp. 7821-7824, (2000).
Okazaki et al., "A novel Therapy of hematopoletic Malignancy by the Inducers of apoptosis,—Induction by ceramide-", Int. J. Hematolo., vol. 65, p. 40, (1997).
Lavie et al., "Agents that Reverse Multidrug Resistance, Tamoxifen, Verapamil, and Cyclosporin A, Block Glycosphingolipid Metabolism by Inhibiting Ceramide Glycosylation in Human Cancer Cells", The Journal of Biological Chemistry, vol. 272, No. 3, pp. 1682-1687, (1997).
Li et al., "Chemical synthesis of D-ribo-phytosphingosine-1-phosphate, a potential modulator of cellular processes", Journal of Lipid Research, vol. 40, pp. 117-125, (1999).
Cuvillier et al., "Suppression of ceramide-mediated programmed cell death by sphingosine-1-phosphate", Nature, vol. 381, pp. 800-803, (1996).
Spiegel et al., "Sphingolipid metabolism and cell growth regulation", FASEB J., vol. 10, pp. 1388-1397, (1996).
Jo et al., "Synthesis of 1-Substituted-phytosphingosine : Novel Protection of Phytosphingosine", Bull. Korean Chem. Soc., vol. 24, No. 3, pp. 267-268, (2003).
Stoffel et al., "Enzymatic Synthesis of 1-Phosphate Esters of 4t-Sphingenine (Sphingosine), Sphinganine (Dihydrosphingosine), 4-Hydroxysphinganine (Phytosphingosine) and 3-Dehydrospingnanine by Erythrocytes", Hoppe-Seyler's Z. Physiol. Chem., vol. 351, pp. 635-642, (1970).
Lanterman et al., "Characterization of sphingosine kinase (SK) activity in *Saccharomyces cerevisiae* and isolation of SK-deficient mutants", Biochem. J., vol. 332, pp. 525-531, (1998).

*Primary Examiner* — Jake Vu
(74) *Attorney, Agent, or Firm* — Vorys, Sater, Seymour and Pease LLP; Mih Suhn Koh

(57) ABSTRACT

The present invention provides: O-cyclic phytospingosine-1-phosphate (O-C-P1P), N-cyclic phytospingosine-1-phosphate (N-C-P1P), a pharmaceutically acceptable salt thereof, or a solvate thereof; a preparation method therefor; a cosmetic composition comprising the same for preventing hair loss or for growing hair; and a pharmaceutical composition for preventing and treating hair loss or for growing hair.

14 Claims, 9 Drawing Sheets

COMPARISON OF THE EFFECTS OF O-C-P1P AND N-C-P1P ON HAIR GROWTH

EFFECT OF O-C-P1P ON HAIR GROWTH AT VARIOUS CONCENTRATIONS

IN VIVO EFFICACY OF O-C-P1P-CONTAINING PRODUCT (2)

Before application   3-week   5-week   8-week   10-week

Group A

Group B

Group C

PHYTOSPHINGOSINE-1-PHOSPHATE DERIVATIVE, PREPARATION METHOD THEREFOR, AND COMPOSITION FOR PREVENTING AND TREATING HAIR LOSS OR FOR GROWING HAIR COMPRISING SAME

BACKGROUND OF INVENTION

Field of the Invention

The present invention relates to a novel phytospingosine-1-phosphate derivative, a preparation method therefor, and a composition comprising the same for preventing and treating hair loss or for growing hair, and more particularly, to a novel phytospingosine-1-phosphate derivative useful for preventing and treating hair loss or for growing hair, a preparation method therefor, a cosmetic composition comprising the same for preventing hair loss or for growing hair, and a pharmaceutical composition comprising the same for preventing and treating hair loss or for growing hair.

Description of the Related Art

Sphingosine-1-phosphate among sphingo lipids is a physiologically active autocrine molecule that induce a physiological reaction by binding to endothelial differentiation gene, EDG (non-patent literature 1), and are produced by sphingosine kinase and degraded by lyase or sphingosine phosphatase (non-patent literature 2).

The dynamic balance in the amounts of sphingolipid metabolites, e.g., ceramide and sphingosine 1-phosphate, and the control of reverse signal process are important factors in determining the life and death of cells (refer to Non-Patent Document 3). Ceramides have double-sided characters as follows: ceramides existing in an increased amount in cells, e.g., cancer cells, inhibit proliferation of the cancer cells while ceramides existing in an increased amount in cells, e.g., inflammatory cells, worsen inflammatory responses. Recently, new functions of sphingolipids, i.e., involvement of ceramides in apoptosis, cell proliferation inhibition, and neurite formation in the nervous system, and the importance of the structure of sphingomyelin in cellular transportation have been suggested. That is, it is believed that three-dimensional asymmetry in endomembrane and outer membrane of cells and non-uniformity of horizontal structures of sphingolipids are involved in various cellular functions, such as differentiation, proliferation, and secretion. In addition, in regard to new functions of sphingolipids, the presence of a mechanism is suggested in that glucosylceramide is accumulated in cells resistant to anti-cancer agents, the resistant cells converting ceramides, which are apoptosis-inducing factors, into other metabolites, such as glycosphingolipids that are accordingly excluded (refer to Non-Patent Document 4). Therefore, it is believed that changes in the amount of sphingolipids may be likely to be involved in blood tumor or conditions of neurological diseases (refer to Non-Patent Document 5).

In this regard, sphingosine-1-phosphate, which is an important intermediate in the metabolism of sphingosine, exhibits a variety of biological activates, and accordingly, many studies have focused on production, metabolism, action, and synthesis methods of sphingosine-1-phosphate (refer to Non-Patent Document 6). However, studies on phytospingosine-1-phosphate, which serves a comparable role with sphingosine-1-phosphate, are extremely limited, and even if studies on phytospingosine-1-phosphate exist, they mainly focus on in vivo roles of phytospingosine-1-phosphate. Preparation methods of these two substances, i.e., sphingosine-1-phosphate and phytospingosine-1-phosphate, are classified into an enzymatic synthesis method using kinase and a chemical synthesis method. The enzymatic synthesis methods described herein are all limited in terms of identifying a structure of a final product (refer to Non-Patent Documents 7, 8, and 9). Although a relatively large number of studies were made regarding a chemical synthesis method of D-sphingosine-1-phosphate, studies on a chemical synthesis method of D-phytospingosine-1-phosphate e- is found only in three thesis papers (refer to Non-Patent Documents 10, 11, and 14). However, these two synthesis methods are performed in the same manner as in the synthesis method of D-sphingosine-1-phosphate (refer to Non-Patent Documents 12 and 13), except that sphingosine was substituted by phytospingosine to be used as a starting substance.

A synthesis method of D-phytospingosine-1-phosphate according to Reaction Equation 1 below has been disclosed as the first chemical synthesis method (refer to Non-Patent Document 10).

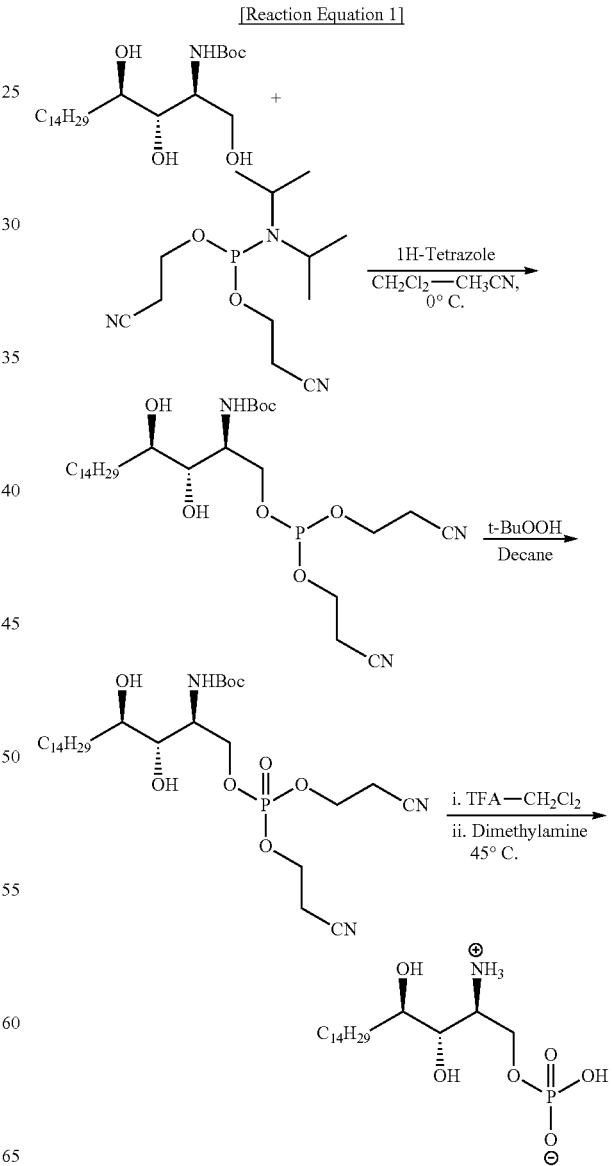

[Reaction Equation 1]

It is reported that the final yield of the entire process of the synthesis method above is about 43%, and there are provided data for high-performance FAB-MS and $^1$H-NMR in regard to the final product, D-phytospingosine-1-phosphate.

Another synthesis method of D-phytospingosine-1-phosphate according to Reaction Equation 2 below has been also disclosed (refer to Non-Patent Document 14).

[Reaction Equation 2]

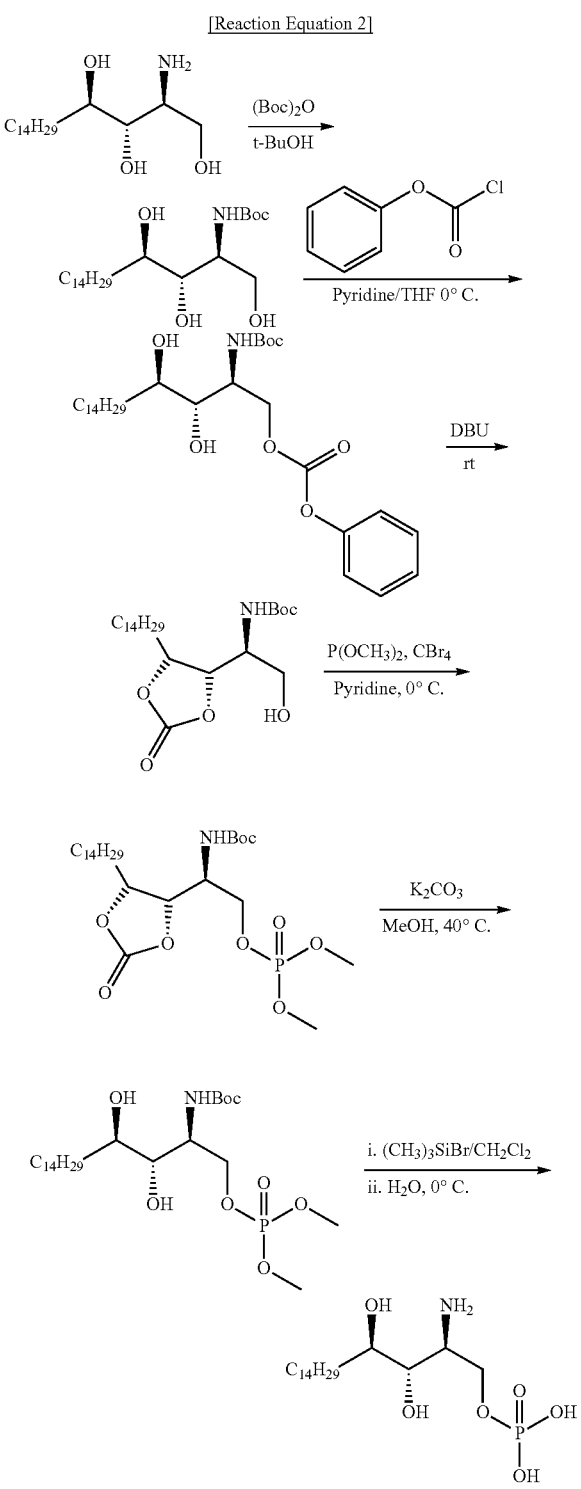

The synthesis methods above consist of 6 steps in total, and it is reported that the final yield of the entire process thereof is about 14.2%. There are provided spectroscopic data for all the intermediates, but detailed spectroscopic data for the final target substance, D-phytospingosine-1-phosphate, is not reported.

Therefore, it is believed that the D-phytospingosine-1-phosphate is a significantly inefficient substance in terms of synthesis thereof since its yield is very low as much as 43% or less according to the synthesis methods above.

The phytospingosine-1-phosphate, which is also recognized as a substance having an equivalent or greater hair growth and restoration efficacy with that of minoxidil, is patented for disclosing use of phytospingosine-1-phosphate derivative for preventing and treating hair loss or for growing hair (refer to Patent document 1). There are various causes of alopecia, i.e., a loss of hair from the scalp, and alopecia can be caused largely by action of male hormones, psychological stress, accumulation of lipid peroxide in the scalp, side effects of drugs, chronic diseases, such as leukemia or tuberculosis, side effects of radiation therapy, malnutrition, and the like. In addition, hair loss that has been known as concerns of the male recently becomes an issue for the female and the young who requiring a large demand for prevention and treatment of hair loss.

Drugs that are currently used for promoting hair growth or that are currently used as hair tonics can be largely divided into vasodilators for circulating sufficient blood to the scalp, female hormones for inhibiting the action of male hormones, and androgen inhibitors for inhibiting 5α-reductase that converts testosterone into 5-dihydrotesteone (5-DHT). Examples of the vasodilators include Carpronium Chloride, minoxidil, and various plant extracts, examples of the female hormones include estrogen, estradiol, and progesterone, and examples of the androgen inhibitors include finasteride and pentadecanoic acid.

However, due to the insufficient efficacy or side effects of the above-described therapeutic agents for hair loss, the development of more effective and safe drugs for treating hair loss or growing hair is needed. In the case of minoxidil used for topical or oral administration, the skin irritation such as scalp redness, inflammation, infection, irritation or pain is caused. In addition, due to the antihypertensive effect of minoxidil, there is a problem of requiring careful administration to patients with hypertension including patients being treated with an antihypertensive drug. In the case of finasteride, due to its inhibitory effects on hormonal activity, it has the disadvantages of erectile dysfunction and decreased sexual desire.

The phytospingosine-1-phosphate derivative is effective to promote angiogenesis, and thus is recognized as a substance with purposes of preventing and treating hair loss or for growing hair. In addition, the phytospingosine-1-phosphate derivative can be used without concerning the side effects of the conventional therapeutic agents for hair loss, the side effects including antihypertensive effects or decreased sexual functions.

However, as described above, the phytospingosine-1-phosphate is a substance having a low synthesis yield, and thus, the development of a substance that can be synthesized in high yields and that is effective in hair loss treatment without the side effects caused by conventional therapeutic agents for hair loss is necessary.

Patent Document

1. Korean Patent 10-1003532

Non-Patent Documents

1. Lee, M. J. et al., Science, 279, pp 1552-1555, 1996
2. Pyne, S. and Pyne, N.J., Biochem. J., 349, pp 385-402, 2000
3. Cuvillier, O. et al., Nature, 381, pp 800-803, 1996
4. Lavie Y. et al., J. Biol. Chem., 272, pp 1682-168'7, 1997
5. Okazaki T. et al., Int. J. Hematolo., 65, p 40, 1997
6. *FASEB J*, 10: 1388-1379
7. *Hoppe-Seyler's Z. Physiol. Chem.*, 351, 635-642,
8. *J Biol. Chem.*, 273, 19437-19442,
9. *Biochem. J.*, 332, 525-531
10. *J. of Lipid Research*, 40, 1999, 117-125
11. *Bull. Korean Chem. Soc.*, 2003, 24, 267-268
12. *J. of Lipid Research*, 35, 1994, 2305-2311
13. *Tetrahedron Letters*, 2000, 41, 7821-7824
14. *Bull. Korean Chem. Soc.*, 2003, 24, 267-268

DETAILED DESCRIPTION OF THE INVENTION

Technical Problem

The present inventors endeavor to developed new active ingredients for treating hair loss that can solve the problems with the conventional therapeutic agents for hair loss, and consequently, and developed a new phytospingosine derivatives that are effective to treat hair loss and to promote grow hair and that can also be synthesized in high yields. In addition, it is confirmed that the present substance is effective not only in treating hair loss and promoting hair growth, but also in wrinkle treatment.

There is provided a novel substance effective to prevent and treat hair loss and to grow hair.

There is provided a method of preparing the novel substance of the present disclosure.

There is provided a cosmetic composition for preventing hair loss or for growing hair, the cosmetic composition comprising the novel substance of the present disclosure.

There is provided a pharmaceutical composition for preventing and treating hair loss and for growing hair, the pharmaceutical composition comprising the novel substance of the present disclosure.

There is provided a cosmetic composition for preventing or smoothing wrinkles, the cosmetic composition comprising the novel substance of the present disclosure.

Technical Solution

To achieve the purposes described above, one aspect of the present invention provides O-cyclic phytospingosine-1-phosphate (O-C-P1P) represented by Formula 1a below or N-cyclic phytospingosine-1-phosphate (N-C-P1P) represented by Formula 1b below, a pharmaceutically acceptable salt of O-C-P1P or N-C-P1P, or a solvate of -C-P1P or N-C-P1P:

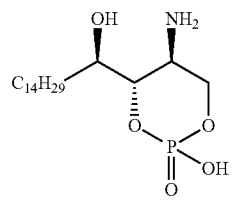
[Formula 1a]

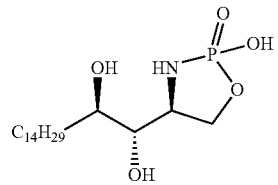
[Formula 1b]

Another aspect of the present invention provides a method of preparing a compound represented by Formula 1a below, the method comprising deprotecting a protecting group of a compound represented by Formula 4 below by performing a reaction with trifluoroacetic acid or concentrated hydrochloric acid:

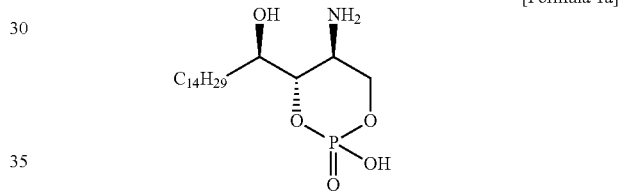
[Formula 1a]

[Formula 4]

wherein, in Formula 4, $R^1$ is a protecting group.

Another aspect of the present invention provides a method of preparing a compound represented by Formula 1b below, the method comprising: performing a reaction between a compound represented by Formula 5 below and bromotrimethylsilane; and performing another reaction by adding water thereto:

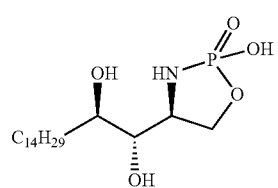
[Formula 1b]

[Formula 5]

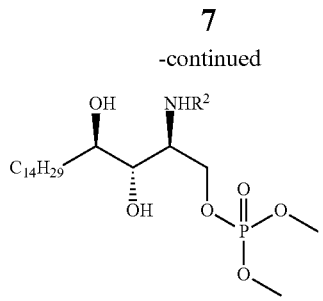

wherein, in Formula 5, R² is a protecting group.

Another aspect of the present invention provides a cosmetic composition for preventing hair loss or for growing hair, the cosmetic composition comprising the compound of Formulae 1a or 1b, the pharmaceutically acceptable salt of the compound of Formulae 1a or 1b, or the solvate of the compound of Formulae 1a or 1b.

Another aspect of the present invention provides a pharmaceutical composition for preventing and treating hair loss or for growing hair, the pharmaceutical composition comprising the compound of Formulae 1a or 1b, the pharmaceutically acceptable salt of the compound of Formulae 1a or 1b, or the solvate of the compound of Formulae 1a or 1b.

Another aspect of the present invention provides a preventing, smoothing, or treating wrinkles, the cosmetic composition comprising the compound of Formulae 1a or 1b, the pharmaceutically acceptable salt of the compound of Formulae 1a or 1b, or the solvate of the compound of Formulae 1a or 1b.

Hereinafter, the present invention will be described in further detail.

All the technical terms used in this specification should be interpreted by the meaning and significance generally known to and understood by anyone skilled in the art, unless defined otherwise. In addition, preferable methods or exemplary embodiments are described in this specification, but methods or exemplary embodiments drawn from their similarities or equivalents come within the scope of the present invention. The contents of all publications used as reference documents in this specification are entirely incorporated by reference in this specification.

As a result of studying for the development substances that can be synthesized in high yields and that are safe and effective for hair loss treatment without concerns of side effects of the conventional therapeutic agents for hair loss, the present inventors developed a compound represented by Formulae 1a or 1b above, as a new derivative of phytospingosine-1-phosphate that is conventionally known as a safe substance.

Accordingly, an aspect of the present invention provides a provides O-cyclic phytospingosine-1-phosphate (O-C-P1P) represented by Formula 1a below or N-cyclic phytospingosine-1-phosphate (N-C-P1P) represented by Formula 1b below, a pharmaceutically acceptable salt of O-C-P1P or N-C-P1P, or a solvate of -C-P1P or N-C-P1P:

[Formula 1a]

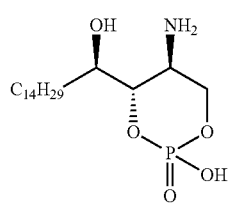

[Formula 1b]

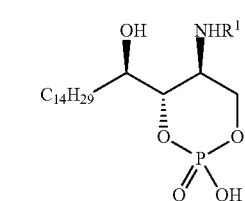

The pharmaceutically acceptable salt may exist as an acid addition salt that forms a salt as well as a free acid by the compound of Formulae 1a or 1b. The compound of Formulae 1a or 1b may form a pharmaceutically acceptable acid addition salt according to a conventional method known in the art. The free acid may be an organic acid or an inorganic acid. Examples of the inorganic acid include hydrochloric acid, bromic acid, or phosphoric acid. Examples of the organic acid include citric acid, acetic acid, lactic acid, tartariac acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, or aspartic acid. In particular, the compound of Formula 1a may be in the form of the hydrochloride.

The pharmaceutically acceptable salt may exist as an inorganic salt of the compound of Formulae 1a or 1b. The compound of Formulae 1a or 1b may form a pharmaceutically acceptable inorganic salt cording to a conventional method known in the art. Examples of the inorganic salt include aluminum, ammonium, calcium, copper, iron, lithium, magnesium, manganese, potassium, sodium, or an zinc-based salt, but the inorganic salt is not limited thereto. Preferable examples of the inorganic slat include ammonium, potassium, magnesium, or a sodium salt.

In addition, the compound of Formulae 1a or 1b according to the present invention may include a solvate comprising not only a pharmaceutically acceptable salt, but also all salts and hydrates that can be prepared according to a conventional method known in the art.

Another aspect of the present invention provides a method of preparing a compound represented by Formula 1a below, the method comprising deprotecting a protecting group of a compound represented by Formula 4 below by performing a reaction with trifluoroacetic acid or hydrochloric acid gas:

[Formula 1a]

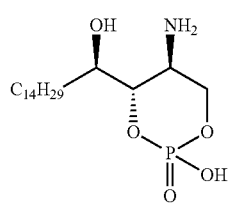

[Formula 4]

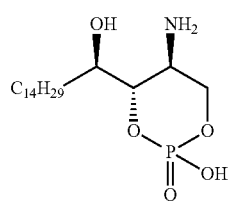

wherein, in Formula 4, R¹ is a protecting group.

In Formula 4, $R^1$ may be, as a protecting group, any protecting group that is conventionally available to protect an amino group, and examples thereof include a t-butyloxycarbonyl group (t-Boc), a p-nitrobenzyloxycarbonyl group, a p-methoxybenzyloxycarbonyl group, or an aryloxycarbonyl group, but $R^1$ is not limited thereto.

Any substance may be used as a solvent for performing the deprotecting of the protecting group of the compound of Formula 4 by performing a reaction with trifluoroacetic acid or hydrochloric acid gas, so long as the solvent does not inhibit the reaction. In a preferable embodiment, methylene chloride may be used in a reaction with trifluoroacetic acid, but ethyl acetate may be used in a reaction with HCl gas. The reaction conditions for the deprotecting may vary according to types of the protecting group and reactants. In an exemplary embodiment, the deprotecting of the protecting group of the compound of Formula 4 may be performed at room temperature in a reaction with trifluoroacetic acid. In another exemplary embodiment, the deprotecting of the protecting group of the compound of Formula 4 may be performed after being cooled to a temperature of about 0° C. in a reaction with HCl gas.

The compound of Formula 4 may be prepared by performing a reaction between a compound represented by Formula 3 below and $POCl_3$:

[Formula 3]

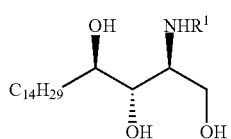

wherein, in Formula 3, $R^1$ is a protecting group.

Any substance may be used as a solvent for performing phosphorylation of the compound of Formula 3 by performing a reaction with $POCl_3$, so long as the solvent does not inhibit the reaction. In a preferable embodiment, pyridine may be used as the solvent. In another preferable embodiment, to perform the reaction with $POCl_3$, the compound of Formula 3 is first dissolved in the pyridine solvent, the mixed solution is cooled to a temperature of about −20° C., and then, a $POCl_3$ solution is added to the pyridine solvent. After completion of the reaction with $POCl_3$, strong acid, such as HCl, may be used to control a pH of the reaction product to about 2, thereby preparing the compound of Formula 4. The compound of Formula 4 prepared therefrom may be utilized to prepare the compound of Formula 1a without performing a particular purification process.

The compound of Formula 3 may be prepared by introducing a protecting group to an amino group of D-phytospingosine represented by Formula 2 below.

[Formula 2]

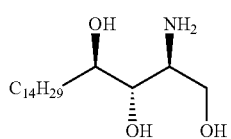

The introducing of the protecting group to the amino group of the D-phytospingosine may be performed according to any method known in the art, e.g., the method described in Non-Patent Document 14.

In an exemplary embodiment, the method of preparing the compound of Formula 1a may be represented by Reaction Equation 3 below.

[Reaction Equation 3]

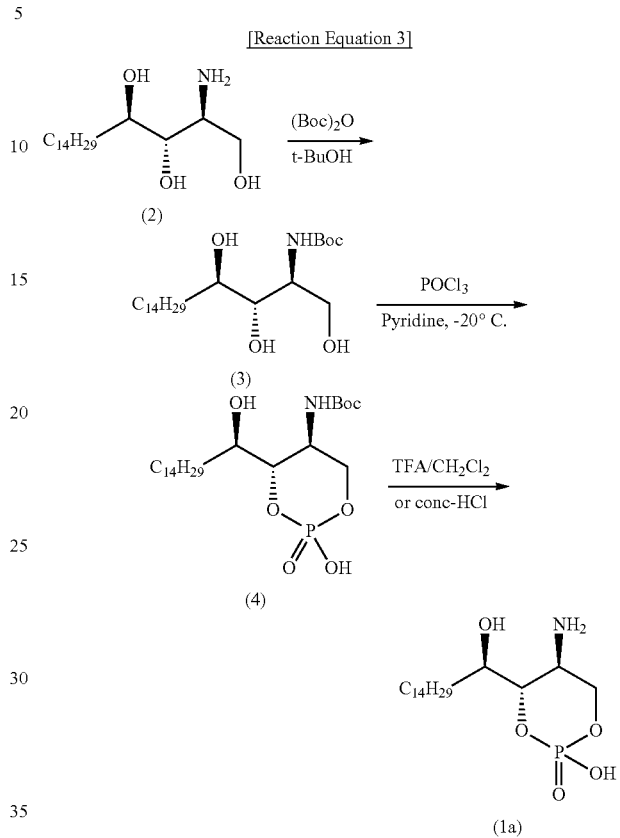

Another aspect of the present invention provides a method of preparing a compound represented by Formula 1b below, the method comprising: performing a reaction between a compound represented by Formula 5 below and bromotrimethylsilane; and performing another reaction by adding water thereto:

[Formula 1b]

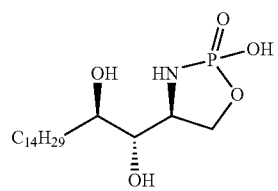

[Formula 5]

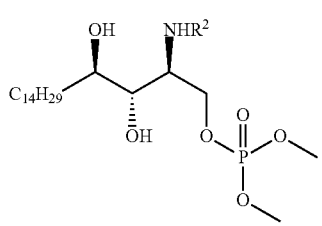

wherein, in Formula 5, $R^2$ is a protecting group.

In Formula 5, $R^2$ may be, as a protecting group, any protecting group that is conventionally available to protect an amino group, and examples thereof include a t-Boc group, a p-nitrobenzyloxycarbonyl group, a p-methoxybenzyloxycarbonyl group, or an aryloxycarbonyl group, but $R^2$ is not limited thereto.

Any substance may be used as a solvent for performing the reaction between the compound of Formula 5 and bromotrimethylsilane, so long as the solvent does not inhibit the reaction. In a preferable embodiment, methylene chloride may be used. The detailed reaction conditions for the deprotecting may vary according to types of the protecting group. In an exemplary embodiment, the compound of Formula 5 is dissolved in a solvent, the mixed solution is cooled to a temperature of about −20° C., and then, bromotrimethylsilane is added thereto. Afterwards, water is added thereto to perform an additional reaction at a temperature of about 0° C., thereby preparing the compound of Formula 1b.

The compound of Formula 5 may be prepared according to any method known in the art, e.g., the method described in Non-Patent Document 14.

In an exemplary embodiment, the method of preparing the compound of Formula 1b may be represented by Reaction Equation 4 below.

[Reaction Equation 4]

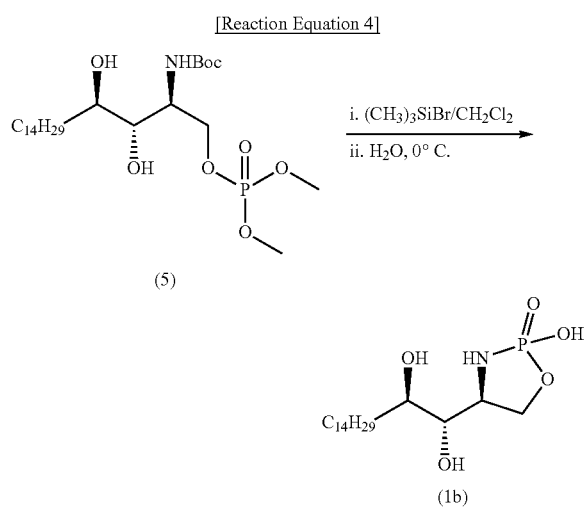

Another aspect of the present invention provides a cosmetic composition for preventing hair loss or for growing hair, the cosmetic composition comprising the compound of Formulae 1a or 1b, the pharmaceutically acceptable salt of the compound of Formulae 1a or 1b, or the solvate of the compound of Formulae 1a or 1b.

Another aspect of the present invention provides a pharmaceutical composition for preventing and treating hair loss or for growing hair, the pharmaceutical composition comprising the compound of Formulae 1a or 1b, the pharmaceutically acceptable salt of the compound of Formulae 1a or 1b, or the solvate of the compound of Formulae 1a or 1b.

Another aspect of the present invention provides a preventing, smoothing, or treating wrinkles, the cosmetic composition comprising the compound of Formulae 1a or 1b, the pharmaceutically acceptable salt of the compound of Formulae 1a or 1b, or the solvate of the compound of Formulae 1a or 1b.

Hereinafter, the cosmetic composition and the pharmaceutical composition will be both referred to as "the composition according to the present invention".

It is confirmed that the compound of Formula 1a (i.e., O-C-P1P) and the compound of Formula 1b (i.e., N-C-P1P) are effective to treat and prevent hair loss and to grow hair in the following Examples. In detail, the compounds according to the present invention are subjected to a hair growth test using a C3H mouse. Consequently, it is confirmed that the compounds according to the present invention exhibit significantly excellent effects on hair growth compared to those of Mynoxyl 3% (minoxidil 3% liquid formulation, Hyundai Pharm), which is a therapeutic agent currently for sale upon the approval by the FDA. In addition, as a result of performing a hair growth test using a C3H mouse with the compounds according to the present invention for each concentration ranging from about 0.005% to about 0.02%, it is confirmed that the compounds according to the present invention exhibit significantly excellent effects compared to those of a negative control group. In addition, there is little difference in effects on hair growth according to each concentration, whereas the compounds according to the present invention exhibit similar effects with those of a positive control group (i.e., minoxidil 3%), Accordingly, it is confirmed that the compounds according to the present invention exhibit excellent effects on hair growth at a concentration that is about 300 times as low as the concentration of the conventional therapeutic agents for hair loss. In addition, as a result of performing a hair growth test using a C3H mouse with the compounds according to the present invention in the form of HCl salts and disodium salts, it is confirmed that the compounds according to the present invention exhibit significantly excellent effects compared to those of a negative control group, regardless of the types of the salts. In addition, as a result of performing a clinical test using the compounds according to the present invention and targeting actual bald patients, effects on hair loss prevention and hair growth are confirmed. Therefore, it is confirmed that the compounds according to the present invention are effective to treat and prevent hair loss and to grow hair.

The cosmetic composition for preventing hair loss or for growing hair and the pharmaceutical composition for preventing and treating hair loss or for growing hair according to the present invention may be used in the form of a combined preparation by further adding other drugs or supplements for preventing and treating hair loss or for growing hair. Examples of the other drugs or supplements include retinoic acid, minoxidil, finasteride, zinc peptide, zinc oxide, biotin, genistein, onion extracts, pumpkin seed oil, Emu oil, green tea extracts, willow bark extracts, extracts of *Centella asiatica*, nettle extracts, extracts of sweet flag, rosemary extracts, or chamomile extracts, but the other drugs or supplements are not limited thereto.

The cosmetic composition for preventing hair loss or for growing hair and the pharmaceutical composition for preventing and treating hair loss or for promoting hair growth or growing hair according to the present invention may be used in the form of oral preparations, injections, suppositories, transdermal preparations, and nasal preparations, but may be also administered in any dosage form that is not limited to the preparations formed described above. Preferably, the compositions may be formulated into preparations suitable for topical application to the scalp or the area of skin where hair grows. Examples of such preparations for topical administration include liposome, nano-emulsion, shampoo, hair conditioner, or hair lotion, but the preparations are not limited thereto. Preferably, to promote effects upon an increase in percutaneous absorption, the compositions may be in a formulation of liposome or nano-emulsion. When formulating the compositions, carriers, diluents, or additives that are known in the field of cosmetics or pharmaceutics and suitable for preparing each formulation may be used.

The cosmetic composition for preventing hair loss or for growing hair and the pharmaceutical composition for preventing and treating hair loss or for growing hair according to the present invention may include the compound of Formulae 1a or 1b in a range of about 0.001 weight % to about 1 weight %, preferable about 0.005 weight % to about 0.1 weight %, based on the total amounts of the composition, wherein the amount of the compound of Formulae 1a or 1b may be increased or decreased according to types of active ingredients. In the case of the pharmaceutical composition according to the present invention for topical administration, the compound of Formulae 1a or 1b may be administered once or two times a day by applying to areas in need of preventing and treating hair loss or of growing hair. The compound of Formulae 1a or 1b may be administered once a day in an amount ranging from about 0.5 mg to about 3 mg based on 1 weight % of the active ingredients, wherein the amount of the compound of Formulae 1a or 1b may be increased or decreased according the size of the application area. Such dosage and frequency of the compound of Formulae 1a or 1b may be appropriately increased or decreased according to patient's age and gender and the progression of hair loss.

Additionally, it is confirmed that the compound of Formula 1a (i.e., O-C-P1P) and the compound of Formula 1b (i.e., N-C-P1P) are effective to prevent, smooth, or treat wrinkles in the following Examples. In detail, the compounds according to the present invention are treated in accordance of concentrations, and then, are subjected to measure proliferation of human fibroblasts through the MTT assay and to measure amounts of collagen in the human fibroblasts. Consequently, it is confirmed that as the concentration of the compounds of the present invention is increased, the viability of the human fibroblasts is increased as well as the amount of the collagen therein. Accordingly, it is confirmed that the compounds according to the present invention are effective to prevent, smooth, and treat wrinkles.

The cosmetic composition for preventing, smoothing, and treating wrinkles according to the present invention may be used in the form of a combined preparation by further adding other substances for preventing, smoothing, and treating wrinkles.

The cosmetic composition for preventing, smoothing, and treating wrinkles according to the present invention may be formulated into preparations suitable for topical application to wrinkled skin or wrinkle prone skin. Examples of such preparations for topical administration include liposome or nano-emulsion, but the preparations are not limited thereto. When formulating the composition, carriers, diluents, or additives that are known in the field of cosmetics suitable for preparing each formulation may be used.

The cosmetic composition for preventing, smoothing, and treating wrinkles according to the present invention may include the compound of Formulae 1a or 1b in a range of about 0.001 weight % to about 1 weight %, preferable about 0.005 weight % to about 0.1 weight %, based on the total amounts of the composition, wherein the amount of the compound of Formulae 1a or 1b may be increased or decreased according to types of active ingredients. In the case of the pharmaceutical composition according to the present invention for topical administration, the compound of Formulae 1a or 1b may be administered once or two times a day by applying to areas in need of preventing, smoothing, and treating wrinkles. The compound of Formulae 1a or 1b may be administered once a day in an amount ranging from about 0.5 mg to about 3 mg based on 1 weight % of the active ingredients, wherein the amount of the compound of Formulae 1a or 1b may be increased or decreased according the size of the application area. Such dosage and frequency of the compound of Formulae 1a or 1b may be appropriately increased or decreased according to patient's age and gender and the progression of wrinkles.

Advantageous Effects of the Invention

As described above, the compound of Formulae 1a or 1b, the pharmaceutically acceptable salt of the compound of Formulae 1a or 1b, or the solvate of the compound of Formulae 1a or 1b according to the present invention exhibit excellent effects to treat and prevent hair loss or to grow hair, and effects to prevent, smooth, or treat wrinkles. Furthermore, the compound of Formulae 1a or 1b, the pharmaceutically acceptable salt of the compound of Formulae 1a or 1b, or the solvate of the compound of Formulae 1a or 1b according to the present invention are economical for being easily prepared by synthesis methods, and can be easily transported to hair follicles when formulated in the form of lipid microspheres such as liposome and nano-emulsion. In addition, compared to other therapeutic agents for hair loss, e.g., minoxidil and finasteride, that have been conventionally used, the compound of Formulae 1a or 1b, the pharmaceutically acceptable salt of the compound of Formulae 1a or 1b, or the solvate of the compound of Formulae 1a or 1b according to the present invention preferably causes no skin irritation and has no side effect.

Figure 1:
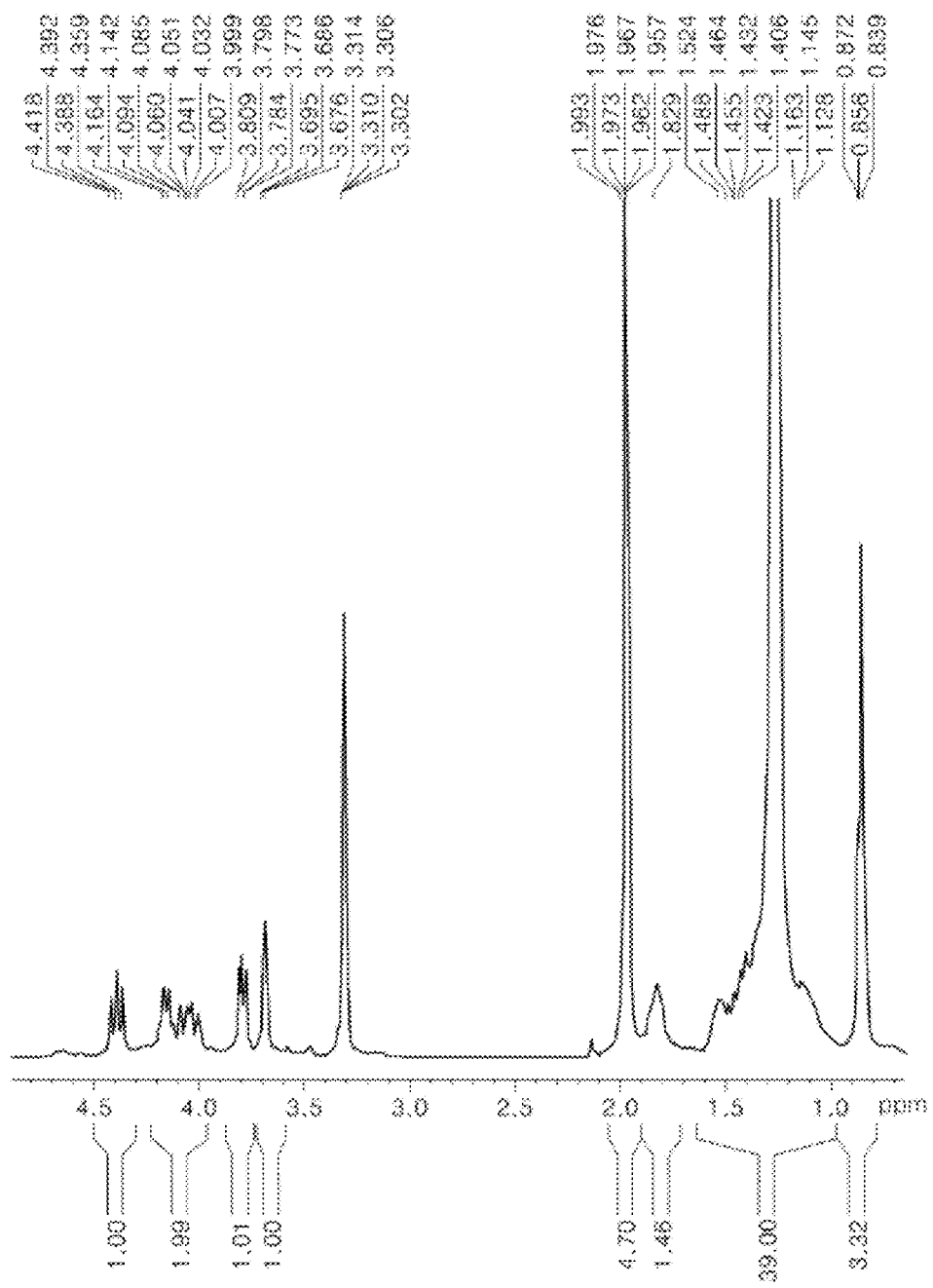
FIG. 1 is a $^1$H NMR spectrum of a compound represented by Formula 1a (i.e., O-cyclic phytospingosine-1-phosphate) prepared according to an exemplary embodiment of the present invention.

Hereinafter, the present disclosure is further explained in more detail with reference to the following examples. These examples, however, should not be interpreted as limiting the scope of the present invention in any manner.

EXAMPLES

Example 1: Preparation of N-Boc-D-phytospingosine

D-phytospingosine was reacted with $(Boc)_2O$ in t-butanol according to the method described in *Bull. Korean Chem. Soc.*, 2003, 24, 267-268, so as to introduce a protecting group (Boc) to an amino group, thereby preparing N-Boc-D-phytospingosine.

Example 2: Preparation of N-Boc-D-phytospingosine-3-O,P-cyclophosphate 1.05 equivalents of $POCl_3$ was slowly added dropwise to a pyridine solvent that was cooled to about –30° C. (up to about ⅓ of the total volume), so as to prepare a $POCl_3$/pyridine solution. Then, the N-Boc-D-phytospingosine (1 equivalent) of Example 1 was dissolved in a pyridine solvent (up to about ⅔ of the total volume), and then, the mixed solution was cooled to a temperature of about –20° C. While maintaining the same temperature, the $POCl_3$/pyridine solution was added thereto. When the reaction temperature rose to room temperature, the pyridine solvent was removed under reduced pressure, and 6N HCl was used to adjust the solution from which the pyridine solvent was removed to have a pH of 2, and then, the solution having a pH of 2 was extracted with ethyl acetate. Afterwards, moisture was removed from an ethyl acetate extract by using $MgSO_4$, and the solvent was concentrated under reduced pressure, so as to quantitatively obtain a desired substance, N-Boc-D-phytospingosine-3-O,P-cyclophosphate. N-Boc-D-phytospingosine-3-O,P-cyclophosphate obtained therefrom was used, without performing an additional purification process, as a starting material in Examples 3 and 4.

Example 3: Preparation of O-cyclic phytospingosine-1-phosphate (Formula 1a) (1)

N-Boc-D-phytospingosine-3-O,P-cyclophosphate of Example 2 was dissolved in $CH_2Cl_2$, and then, the mixed solution was added to a $CH_2Cl_2$ solvate using trifluoroacetate up to about ⅓ of the total volume of the $CH_2Cl_2$ solvate. The mixed solution was then stirred at room temperature for 1 hour. Afterwards, the solvate was removed from the mixed solution under reduced pressure, and then, a Conc-HCl solvate was added thereto to be strongly stirred. White solids produced therefrom were filtered, washed subsequently with water and acetone, and then, dried, so as to obtain a final desired product, O-cyclic phytospingosine-1-phosphate (O-C-P1P) in the form of a HCl salt (total yield: 90%).

Example 4: Preparation of O-cyclic phytospingosine-1-phosphate (Formula 1a) (2)

N-Boc-D-phytospingosine-3-0,P-cyclophosphate of Example 2 was dissolved in an ethylacetate solvate, and then, the mixed solution was cooled to a temperature of about 0° C. Then, HCl gas was injected thereto for 1 hour. White solids produced therefrom were filtered, washed with ethyl acetate, and then, dried, so as to obtain a final desired product, O-cyclic phytospingosine-1-phosphate (O-C-P1P) in the form of a HCl salt (total yield: 93%).

Data obtained from $^1H$ NMR (300 MHz, $CD_3OD$:$CD_3COOD$=1:1) spectra of the finally obtained product is shown in FIG. 1

The obtained HCl salt was treated with a KOH ethanol solution of the same equivalent with the HCl salt, so as to obtain O-cyclic phytospingosine-1-phosphate from which the HCl salt was removed.

In addition, the obtained O-C-P1P was treated with 3 equivalents of a NaOH aqueous solution, so as to prepare a disodium salt of O-C-P1P.

Example 5: Preparation of N-cyclic phytospingosine-1-phosphate (Formula 1b)

N-Boc-D-phytospingosine-1-phosphoric acid ester was prepared according to the method described in *Bull. Korean Chem. Soc.*, 2003, 24, 267-268. The prepared N-Boc-D-phytospingosine-1-phosphoric acid ester was dissolved in $CH_2Cl_2$, and then, the mixed solution was cooled to a temperature of about –20° C. Afterwards, 5 equivalents of bromo dimethyl silane were added thereto to be stirred for about 1 hour. Then, water was added thereto to perform heating concentration, and acetone was added to residues obtained from the heating concentration. White solids obtained therefrom were filtered, so as to obtain a title compound (i.e., N-C-P1P) (total yields: 13%).

Figure 2:
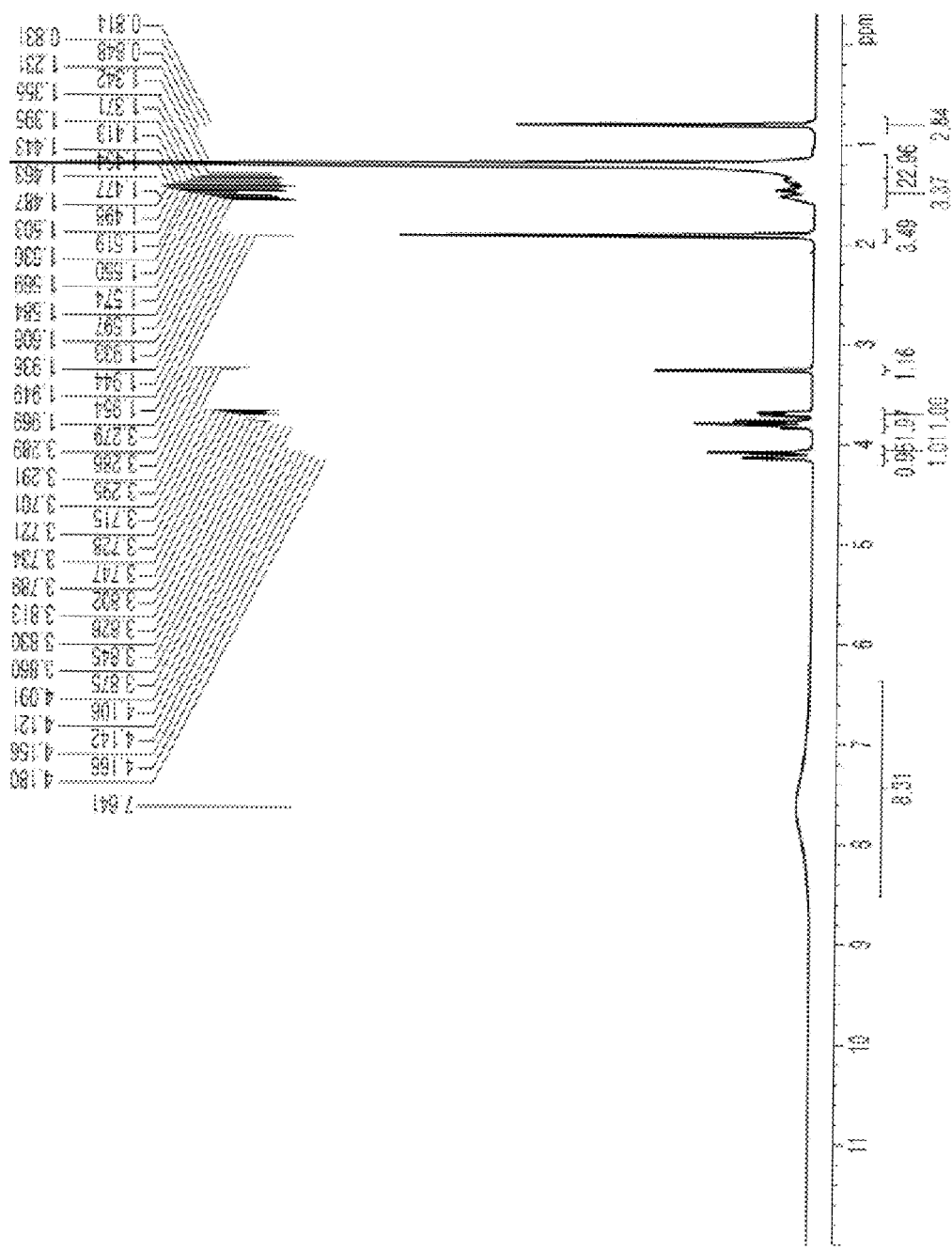
FIG. 2 is a $^1$H NMR spectrum of a compound represented by Formula 1b (i.e., N-cyclic phytospingosine-1-phosphate) prepared according to an exemplary embodiment of the present invention.

Data obtained from $^1H$ NMR (300 MHz, $CD_3OD$:$CD_3COOD$=1:1) spectra of the finally obtained product is shown in FIG. 2.

Example 6: Preparation of O-C-P1P-Containing Liposome

First, 1 g of 75% soybean phosphatidylcholine (available by Lipoid Company), 0.01 g of O-C-P1P of Example 4, and 0.3 g of vitamin E acetate were dissolved in a mixed solution of 20 g of ethanol and 2 g of ethoxydiglycol, so as to prepare an O-C-P1P ethanol solution. The obtained solution was ultrasonically treated for 5 minutes for dissolution. Next, an aqueous solution in which 0.5 g of menthol, 0.5 g of niacin amide, 3 g of natural organic sulfur, and 0.1 g of hesperidin were dissolved in 71.59 g of distilled water was slowly added to the O-C-P1P ethanol solution. Here, the mixed solution was strongly stirred. After finishing the addition of distilled water, the mixed solution was continuously stirred for 30 minutes. Then, a bath-type sonicator was used to perform ultrasonic treatment thereon for 30 minutes, so that the particles had a particle diameter of about 100 nm, thereby preparing liposome containing O-C-P1P.

Separately, when preparing liposome according to the preparation method described above, as a skin penetration promoter, a mixture of poloxamer+polysorbate 80 (Tween 80) was added, thereby preparing liposome for promoting skin penetration.

Example 7: Preparation of O-C-P1P-Containing Liposome (2)

Liposome containing O-C-P1P was prepared in the same manner as in Example 6, except that in preparing the aqueous solution, 1 g of willow bark extracts, 1 g of green tea extracts, 3 g of *C. asiatica* extract, 0.5 g of nettle extracts, 0.5 g of sweet flag extracts, 0.5 g of rosemary extracts, 0.5 g of chamomile extracts, and 1 g of fermented soybean were additionally added. Here, the liposome was prepared by using a small amount of distilled water for the amounts of each extract added therein.

Example 8: Preparation of N-C-P1P-Containing Liposome (1)

Liposome containing N-C-P1P 0.01% was prepared in the same manner as in Example 6, except that N-C-P1P of Example 5 was used instead of O-C-P1P.

Example 9: Preparation of N-C-P1P-Containing Liposome (2)

Liposome containing N-C-P1P 0.01% was prepared in the same manner as in Example 7, except that N-C-P1P of Example 5 was used instead of O-C-P1P.

The compositions of the liposomes prepared in Examples 6 to 9 are listed in Table 1 below.

TABLE 1

| | Composition of Examples | | | |
|---|---|---|---|---|
| | Example 6 | Example 7 | Example 8 | Example 9 |
| O—C-P1P | 0.01 | 0.01 | 0 | 0 |
| N—C-P1P | 0 | 0 | 0.01 | 0.01 |
| Lecithin | 1 | 1 | 1 | 1 |
| Ethanol | 20 | 20 | 20 | 20 |
| Ethoxydiglycol | 2 | 2 | 2 | 2 |
| Poloxamer | 0.5 | 0.5 | 0.5 | 0.5 |
| Tween 80 ® | 0.5 | 0.5 | 0.5 | 0.5 |
| Niacin amide | 0.5 | 0.5 | 0.5 | 0.5 |
| Menthol | 0.5 | 0.5 | 0.5 | 0.5 |
| Natural organic sulfur | 3 | 3 | 3 | 3 |
| Hesperidin | 0.1 | 0.1 | 0.1 | 0.1 |
| Green tea extracts | 0 | 1 | 0 | 1 |
| willow bark extracts | 0 | 1 | 0 | 1 |
| Fermented soybean | 0 | 1 | 0 | 1 |
| *C. asiatica* extracts | 0 | 3 | 0 | 3 |
| Nettle extracts | 0 | 0.5 | 0 | 0.5 |
| Sweet flag extracts | 0 | 0.5 | 0 | 0.5 |
| Rosemary extracts | 0 | 0.5 | 0 | 0.5 |
| Chamomile extracts | 0 | 0.5 | 0 | 0.5 |
| Distilled water | 71.89 | 63.89 | 71.89 | 63.89 |

Experimental Example 1: Hair Growth Test Using C3H Mice (1)

A 6-week C3H mouse was purchased, and the hair on a dorsal part of the mouse was partially removed. Then, hair removal cream was applied to the dorsal part to completely remove the existing hair. A mouse of which the hair was not completely removed was excluded from the test. After finishing the hair removal, 5 mice were randomly bred per cage, and a total of 5 cages were used.

The mice were left one day or so after finishing depilation, and a test compound, which was prepared by dissolving O-C-P1P of Example 4 and N-C-P1P of Example 5 in a mixed solution of ethanol and ethoxydiglycol (9:1, v/v) to a concentration of 0.01 weight %, was applied once a day to the area from which the hair was removed. A negative control group was prepared by applying a mixed solution of ethanol and ethoxydiglycol without using the test compound, and a positive control group was 3% minoxidil preparation (Mynoxyl, Hyundai Pharm). After applying samples to the area from which the hair was removed, images of the area captured at the $14^{th}$ and $18^{th}$ days are shown in FIG. 3.

Figure 3:
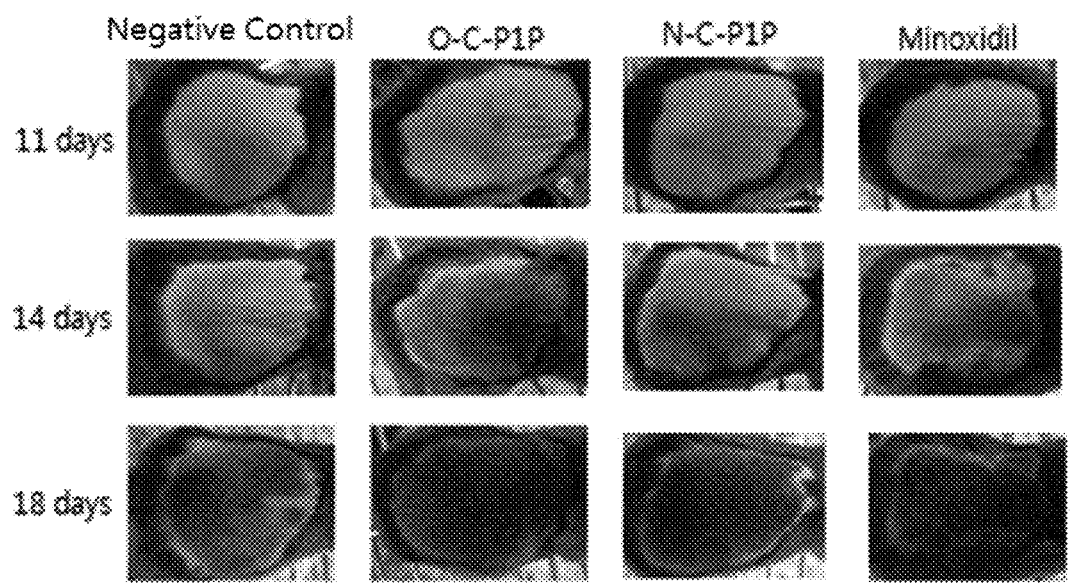
FIG. 3 shows images of the skin treated with the present compounds, a positive (3% minoxidil liquid) control or a negative control. The images were obtained at the $11^{th}$, $14^{th}$, and $18^{th}$ days after applying the O-C-P1P or N-C-P1P solution according to the present invention once a day to the shaved flank of C3H mice.

Referring to FIG. 3, it was confirmed that hair hardly grew on the area in a non-treated group (i.e., negative control group), resulting in the exposure of the skin to the outside, whereas a rapid growth of hair was made in the O-C-P1P-treated group and the N-C-P1P-treated group. In detail, the effects on faster hair growth were shown better in the O-C-P1P-treated group than in the positive control group. Although the effects on hair growth were quite less in the N-C-P1P-treated group than in the positive control group, the effects were significantly better in the N-C-P1P-treated group than in the negative control group. Therefore, based on the results above, it was clearly confirmed that the compounds according to the present invention were effective to promote hair growth.

Experimental Example 2: Hair Growth Test Using C3H Mice (2)

A hair growth test was performed in the same manner as in Experimental Example 1 by using the liposomes containing O-C-P1P as prepared according to Examples 6 and 7, and the test compounds were continuously applied once a day for 3 weeks. Images of the area from which the hair was removed were captured, and the captured images are shown in FIG. 4.

Figure 4:
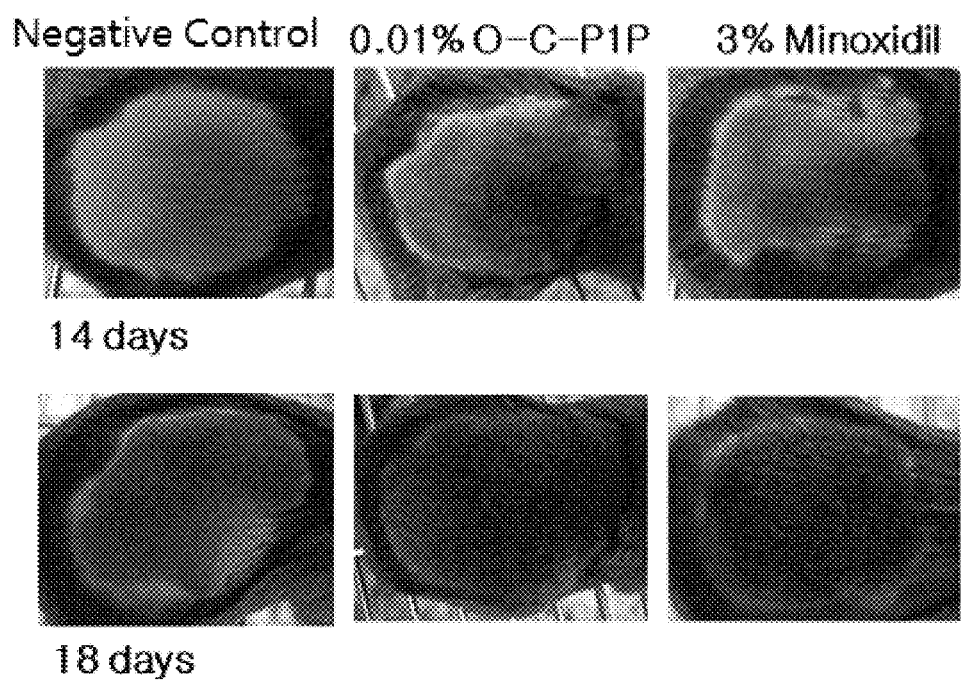
FIG. 4 shows images of the skin treated with the present compound, positive and negative controls, the images were obtained at the $14^{th}$ and $18^{th}$ days after applying O-C-P1P liposome according to the present invention once a day to the shaved flank of C3H mice.

Referring to FIG. 4, it was confirmed that the O-C-P1P-treated group had significant effects on hair growth compared to those of the negative control group, that the O-C-P1P-treated group had similar effects on hair growth with those of the positive control group.

Experimental Example 3: Hair Growth Test Using Various Concentrations of O-C-P1P (3)

O-C-P1P of Example 4 was dissolved in a mixed solution of ethanol and ethoxydiglycol (9:1, v/v) at three different concentrations, i.e., 0.005 weight %, 0.01 weight %, and 0.02 weight %, so as to prepare three different samples. Then, a hair growth test using these samples was performed in the same manner as in Text Example 1.

Figure 5:
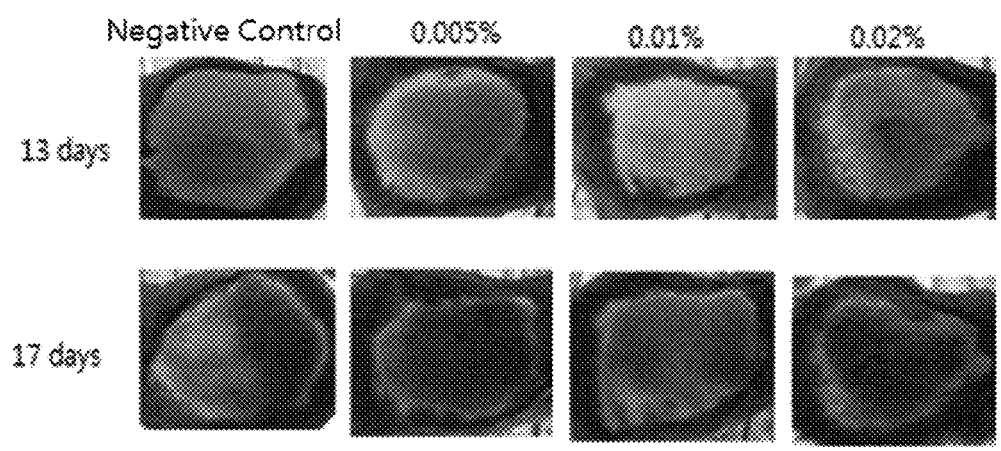
FIG. 5 shows images of the skin treated with various concentrations of the present compound and negative control, the images were obtained at the $13^{th}$ and $17^{th}$ days after applying various concentrations of O-C-P1P solution according to the present invention once a day for each concentration to the shaved flank of C3H mice.

After applying the samples to the area from which the hair was removed, images of the area captured at the $13^{th}$ and $17^{th}$ days are shown in FIG. 5.

Referring to FIG. 5, it was confirmed that the O-C-P1P-treated groups at different concentrations (from 0.005 weight % to 0.02 weight %) showed significant effects on hair growth compared to those of the negative control group. However, there was no significant different in the effects on hair growth among the C-P1P-treated groups at different concentrations (0.005 weight %, 0.01 weight %, and 0.02 weight %). Such results are also similarly shown in a group administered with 3% minoxidil preparations (3 weight %), and accordingly, it was confirmed that O-C-P1P exhibits the same effects on hair growth at a concentration that is about 300 times as low as the concentration of minoxidil.

Experimental Example 4: Hair Growth Test Using Various Salts of O-C-P1P

A hair growth test was performed in the same manner as in Experimental Example 1 by using the salts of O-C-P1P as synthesized in Example 4, O-C-P1P as prepared in Example 4, and the disodium salts of O-C-P1P as synthesized in Example 4.

Figure 6:
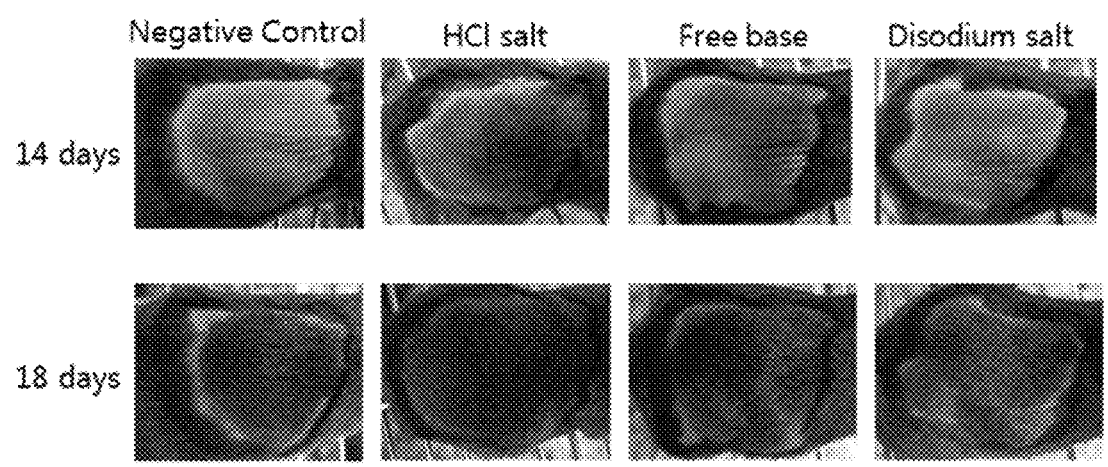
FIG. 6 shows images of the skin treated with various salts of the present compound and negative control, the images was obtained at the $14^{th}$ and $18^{th}$ days after applying an O-C-P1P free base, an HCl salt of O-C-P1P, and a solution containing a disodium salt of O-C-P1P according to the present invention once a day to the shaved flank of C3H mice.

After the samples to the area from which the hair was removed, images of the area captured at the $14^{th}$ and $18^{th}$ days are shown in FIG. 6.

Referring to the results of FIG. 6, it was confirmed that the negative control group showed significant effects on hair growth regardless of the types of the salts.

Experimental Example 5: Efficacy of the Present Compound on Hair Growth in Clinical Trials (1)

The liposome containing O-C-P1P as prepared in Example 7 was directly applied to applicants having hair loss in progression, so as to compare hair growth efficacy. The application was performed once or twice a day on two applicants, and more particularly, the liposome was sprayed 5 to 7 times for each application, and then, the liposome-sprayed part was rubbed by hands to prevent the liposome solution from being flown down.

Figure 7A:
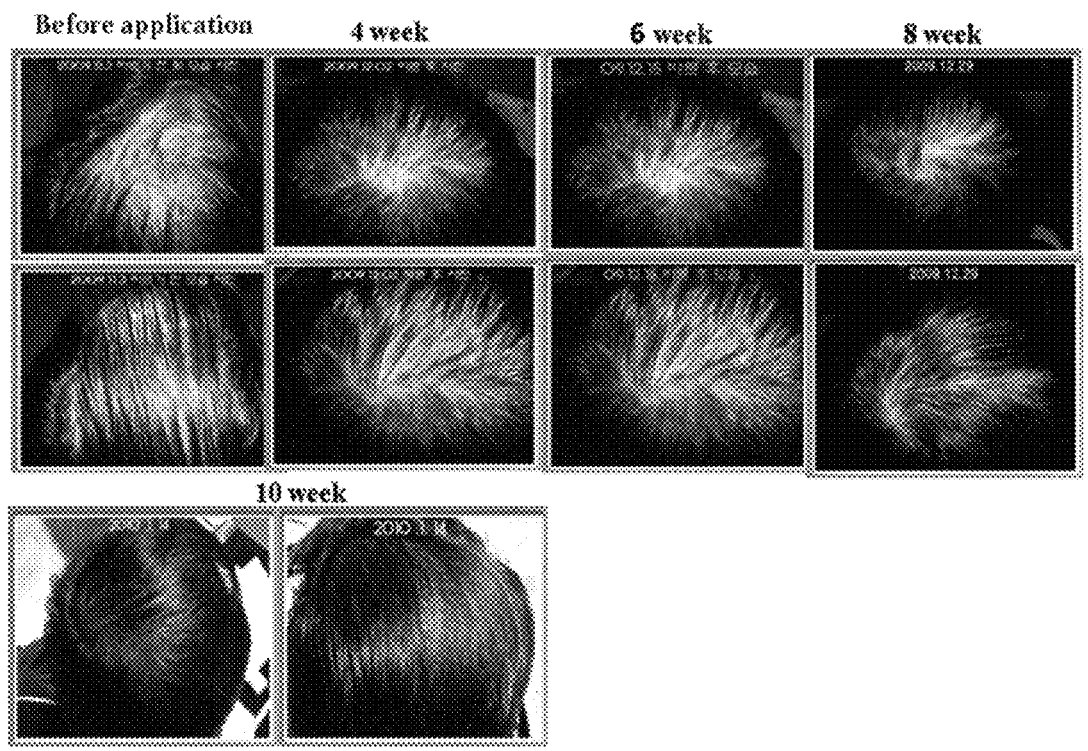
FIGS. 7A and 7B are images of the top of the head treated with the present compound showing the hair growth with time. The images were obtained at the indicated weeks after applying the O-C-P1P liposome according to the present invention once or two times a day to a subject having hair loss in progression
Figure 7B:
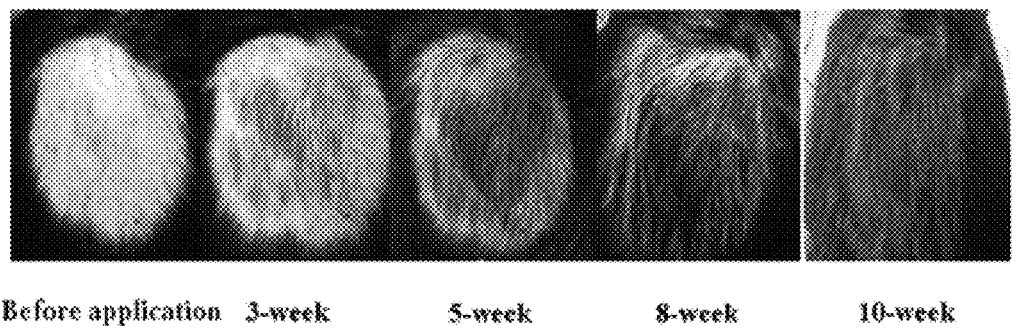

Images of the head captured before applying the sample and images of the head captured with lapse of time are shown in FIGS. 7A and 7B.

Referring to FIGS. 7A and 7B, it was confirmed that the case where the sample was applied with lapse of time showed excellent effects on prevention of hair loss and on hair growth compared to the case where the sample was not applied yet. That is, once directly applied to the human body, excellent effects on prevention of hair loss and on hair grown can be found.

Experimental Example 6: Efficacy of the Present Compound on Hair Growth in Clinical Trials (2)

O-C-P1P liposomes at different concentrations, i.e., 0.002 weight % (Group A), 0.01 weight % (Group B), and 0.05 weight % (Group C), were prepared as described in Example 7, and then, these samples were directly applied to applicants having hair loss in progression, so as to compare hair growth efficacy. Here, the results were compared according to a double blind test not to let a test subject person and an experimenter know the different concentrations of the samples.

Figure 8:
FIG. 8 shows images of the scalp before and 16 weeks after applying the O-C-P1P liposome in various concentrations, the images were obtained in a clinical test performed on the subject having hair loss in progression by applying to the subject the O-C-P1P liposome according to the present invention in an amount of 0.002 weight % (Group A), 0.01 weight % (Group B), and 0.05 weight % (Group C) in a double blind test.
Figure 8:
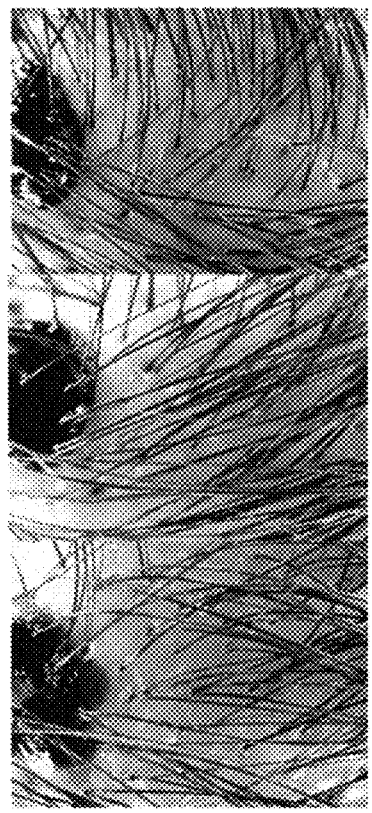

For a period of 4, 8, 12, and 16 weeks after applying the samples, changes in density and thickness of the hair were observed, so as to evaluate clinical efficacy according to the different concentrations of O-C-P1P. The results obtained by observing changes in density and thickness of the hair for each concentration are summarized in Tables 2 and 3 below. The evaluation was made in the following manner (unit: evaluation unit for scalp thickness and thickness, 0: no change, 1: improved at a perceptible level, 2: slightly improved, 3: improved, 4: appreciably improved, 5: significantly improved). Images of the hear captured before applying the sample and images of the hear captured at the $16^{th}$ weeks after applying the sample were compared according to Groups each having different concentrations, and the comparative results are shown in FIG. 8

TABLE 2

Changes in hair density during a period of 16 weeks

| | Average | | | |
|---|---|---|---|---|
| | 0 week | 8 weeks | 12 weeks | 16 weeks |
| Group A | 0 | 0.17 | 1.08 | 1.92* |
| Group B | 0 | 0.22 | 2.00* | 2.78* |
| Group C | 0 | 1.11 | 1.78* | 2.78* |

*Data having statistical significance

TABLE 3

Changes in hair thickness during a period of 16 weeks

| | Average | | | |
|---|---|---|---|---|
| | 0 week | 8 weeks | 12 weeks | 16 weeks |
| Group A | 0 | 0.00 | 0.17 | 0.42 |
| Group B | 0 | 0.11 | 0.78 | 1.33* |
| Group C | 0 | 0.11 | 0.78 | 1.56* |

*Data having statistical significance

Referring to Tables 2 and 3 above, it was confirmed that Groups B and C showed statistically significant changes in density and thickness of the hair at the $12^{th}$ and $16^{th}$ weeks. In addition, referring to FIG. 8, the case where the sample was applied showed increased density of the hair compared to the case where the sample was not applied yet.

Experimental Example 7: Promotion of Cell Proliferation and Collagen Synthesis

To measure anti-wrinkle effects of N-C-P1P and O-C-P1P, effects of human fibroblasts on cell proliferation were measured via an MTT (3-[4,5-dimethylthiazol-2-yl]-2,5-diphenyltetrazolium bromide) assay. To observe collagen synthesis, procollagent type I, which is produced in human fibroblasts (e.g., dermal cells), were measured.

To measure cell proliferation, human fibroblasts were cultured for 24 hours in a Dulbecco's modified eagle medium (DMEM) medium supplemented with 10% FBS and 100 unit/mL of penicillin/streptomycin. The culture circumstances comprising culturing in a 5% $CO_2$ incubator maintained at a temperature of 37° C. Then, after removing the medium therefrom, N-C-P1P and O-C-P1P were added thereto at different concentrations. The MTT assay was performed to measure effects of N-C-P1P and O-C-P1P on cell proliferation, and the results are summarized in Table 4.

TABLE 4

Effects on cell proliferation by N-C-P1P and O-C-P1P

| Concentration | Cell Viability (%) | | | | |
|---|---|---|---|---|---|
| Group | 0 | 0.002% | 0.004% | 0.008% | 0.016% |
| N—C-P1P | 100 | 120 | 110 | 110 | 125 |
| O—C-P1P | 100 | 128 | 135 | 143 | 160 |

To measure collagen synthesis, the human fibroblasts (e.g., dermal cells) were cultured in the same conditions as above for 24 hours. After removing the medium therefrom, a new serum free medium was substituted. N-C-P1P and O-C-P1P (1 uM and 10 uM) that were diluted step by step were added to the new medium, and then, the medium was cultured for another 24 hours. The culture medium was used to measure amounts of synthesized collagen by using a procollagen type I C-peptide EIA kit, and the results measured therefrom are shown in Table 5 below.

TABLE 5

Effect on the synthesis of collagen by N-C-P1P and O-C-P1P

| Concentration | Collagen synthesis (%) | | |
|---|---|---|---|
| Group | 0 | 0.1 μM | 1 μM |
| N—C-P1P | 100 | 110 | 125 |
| O—C-P1P | 100 | 120 | 140 |

Referring to the results of Tables 4 and 5, it was confirmed that N-C-P1P and O-C-P1P were capable of not only promoting cell proliferation, but also promoting synthesis of collagen. Therefore, N-C—P1P and O-C-P1P were found to be applicable to anti-aging and anti-wrinkle products that promote proliferation of human fibroblasts and synthesis of collagen.

The invention claimed is:

1. O-cyclic phytospingosine-1-phosphate (O-C-P1P) represented by Formula 1a below or N-cyclic phytospingosine-1-phosphate (N-C-P1P) represented by Formula 1b below, a pharmaceutically acceptable salt of O-C-P1P or N-C-P1P, or a solvate of O-C-P1P or N-C-P1P:

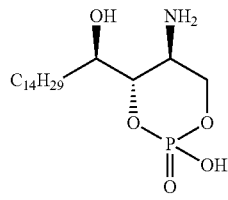

[Formula 1a]

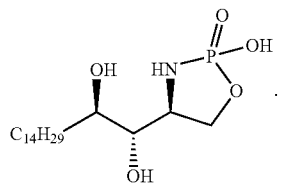

[Formula 1b]

2. A method of preparing a compound represented by Formula 1a below, the method comprising:

deprotecting a protecting group of a compound represented by Formula 4 below by performing a reaction with trifluoroacetic acid or hydrochloric acid (HCl) gas:

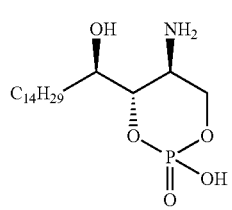

[Formula 1a]

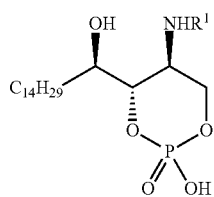

[Formula 4]

wherein, in Formula 4, $R^1$ is a protecting group.

3. The method of claim 2, wherein the compound of Formula 4 is prepared by performing a reaction between a compound represented by Formula 3 below and $POCl_3$:

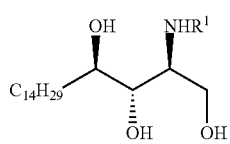

[Formula 3]

wherein, in Formula 3, $R^1$ is a protecting group.

4. The method of claim 3, wherein the compound of Formula 3 is prepared by introducing a protecting group to an amino group of D-phytospingosine represented by Formula 2 below:

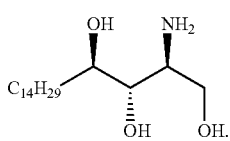

[Formula 2]

5. A method of preparing a compound represented by Formula 1b below, the method comprising:

performing a reaction between a compound represented by Formula 5 below and bromotrimethylsilane; and
performing another reaction by adding water thereto:

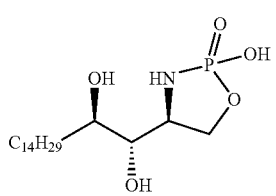

[Formula 1b]

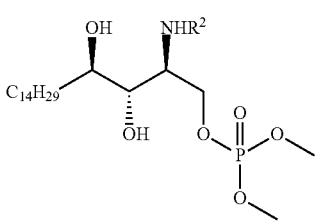

[Formula 5]

wherein, in Formula 5, $R^2$ is a protecting group.

6. A cosmetic composition for preventing hair loss or for promoting hair growth, the cosmetic composition comprising the compound of Formulae 1a or 1b, the pharmaceutically acceptable salt of the compound of Formulae 1a or 1b, or the solvate of the compound of Formulae 1a or 1b according to claim 1.

7. A pharmaceutical composition for preventing and treating hair loss or for promoting hair growth, the pharmaceutical composition comprising the compound of Formulae 1a or 1b, the pharmaceutically acceptable salt of the compound of Formulae 1a or 1b, or the solvate of the compound of Formulae 1a or 1b according to claim 1.

8. The composition of claim 6, wherein the composition is a preparation suitable for a topical application to a scalp or the area of skin where hair grows.

9. The composition of claim 8, wherein the composition is in a formulation of liposome, nano-emulsion, shampoo, hair conditioner, or hair lotion.

10. A cosmetic composition for preventing, smoothing, or treating wrinkles, the cosmetic composition comprising the compound of Formulae 1a or 1b, the pharmaceutically acceptable salt of the compound of Formulae 1a or 1b, or the solvate of the compound of Formulae 1a or 1b according to claim 1.

11. The cosmetic composition of claim 10, wherein the composition is a preparation suitable for topical application on wrinkled skin or wrinkle prone skin.

12. The cosmetic composition of claim 11, wherein the composition is in a formulation of liposome or nano-emulsion.

13. The composition of claim 7, wherein the composition is a preparation suitable for a topical application to a scalp or the area of skin where hair grows.

14. The composition of claim 7, wherein the composition is in a formulation of liposome, nano-emulsion, shampoo, hair conditioner, or hair lotion.

* * * * *